United States Patent [19]

Bryant et al.

[11] 4,283,304

[45] Aug. 11, 1981

[54] PROCESS FOR REMOVING TRIORGANOPHOSPHINE FROM A LIQUID COMPOSITION

[75] Inventors: David R. Bryant; Richard A. Galley, both of South Charleston, W. Va.

[73] Assignee: Union Carbide Corporation, New York, N.Y.

[21] Appl. No.: 108,279

[22] Filed: Dec. 28, 1979

Related U.S. Application Data

[63] Continuation-in-part of Ser. No. 40,913, May 21, 1979, abandoned.

[51] Int. Cl.$^3$ .................. B01J 31/40; B01J 31/24; C07F 9/50; C07C 45/50
[52] U.S. Cl. .................. 252/413; 252/412; 252/414; 252/431 P; 260/429 R; 568/17; 568/454
[58] Field of Search .............. 252/412, 413, 414, 420, 252/431 P; 260/429 R; 568/454, 17; 423/22

[56] References Cited

U.S. PATENT DOCUMENTS

| | | | |
|---|---|---|---|
| 2,822,376 | 2/1958 | Hechenbleikner et al. | 260/465.1 |
| 3,527,809 | 9/1970 | Pruett et al. | 568/454 |
| 3,555,098 | 1/1971 | Olivier et al. | 568/454 |
| 3,968,134 | 7/1976 | Gregorio et al. | 260/429 R |
| 4,009,003 | 2/1977 | Stautzenberger et al. | 23/230 |
| 4,148,830 | 4/1979 | Pruett et al. | 568/454 |
| 4,151,209 | 4/1979 | Paul et al. | 568/454 |

OTHER PUBLICATIONS

"*Ylid Chemistry*", A. W. Johnson, Academic Press, N.Y., pp. 39–43 (1966).
"*The Chemistry of Phosphorous*", J. Elmsley & D. Hall, Harper & Rowe Ltd., London, England, pp. 126–142 (1976).
"*Acta Chem. Scanda*", vol. 15, pp. 692–694 (1961).
"Helvetica Chimica Acta", vol. 46, pp. 2178–2185 (1963).
Houben Weyl's Encyclopedia, "Methoden der Organischen Chemie", 4th Edition, vol. XII, part I, (1963), Georg Thieme publisher.
Stuttgart, DE, concerning the chapter on "Organische Phosphorverbindingen", pp. 92, 111 and 112.

*Primary Examiner*—P. E. Konopka
*Attorney, Agent, or Firm*—Reynold J. Finnegan

[57] ABSTRACT

Process for removing triorganophosphine from a rhodium containing composition or a rhodium containing concentrate thereof.

43 Claims, No Drawings

PROCESS FOR REMOVING TRIORGANOPHOSPHINE FROM A LIQUID COMPOSITION

This application is a continuation-in-part of U.S. Application Ser. No. 40,913 filed May 21, 1979, now abandoned.

FIELD OF THE INVENTION

This invention relates to a process for removing triorganophosphine from a rhodium containing composition or a rhodium containing concentrate thereof. More particularly this invention relates to a process for removing triorganophosphine from a rhodium containing hydroformylation reaction medium or a rhodium containing concentrate thereof.

BACKGROUND OF THE INVENTION

Processes for forming an aldehyde by the reaction of an olefin with carbon monoxide and hydrogen in the presence of a solubilized solution of a Group VIII metal-trihydrocarbyl ligand complex catalyst are well known in the art.

In more recent developments the preferred Group VIII metal has been rhodium, while the preferred trihydrocarbyl ligand has been triarylphosphine such as triphenylphosphine.

For instance, U.S. Pat. No. 3,527,809, the entire disclosure of which is incorporated herein, discloses a hydroformylation process whereby alpha-olefins are hydroformylated with carbon monoxide and hydrogen to produce aldehydes in high yields at low temperatures and pressures, where the normal to iso-(or branched-chain) aldehyde isomer ratio of the product aldehydes is high. This process employs certain rhodium complex catalysts and operates under defined reaction conditions to accomplish the olefin hydroformylation and since this process operates at significantly low pressures, substantial advantages were realized including lower initial capital investment and lower operating costs. Further, the more desirable straight chain aldehyde isomer can be produced in high yields.

The hydroformylation process set forth in said U.S. Pat. No. 3,527,809 noted above includes the following essential reaction conditions:

(1) A rhodium complex catalyst which is a complex combination of rhodium with carbon monoxide and a triorganophosphorus ligand. The term "complex" means a coordination compound formed by the union of one or more electronically rich molecules or atoms capable of independent existence with one or more electronically poor molecules or atoms, each of which is also capable of independent existence. Triorganophosphorus ligands whose phosphorus atom has one available or unshared pair of electrons are capable of forming a coordinate bond with rhodium.

(2) An alpha-olefin feed of alpha-olefinic compounds characterized by a terminal ethylenic carbon-to-carbon bond such as a vinyl group $CH_2=CH-$. They may be straight chain or branched chain and may contain groups or substituents which do not essentially interfere with the hydroformylation reaction, and they may also contain more than one ethylenic bond. Propylene is an example of a preferred alpha-olefin.

(3) A triorganophosphorus ligand such as a triarylphosphine. Desirably each organo moiety in the ligand does not exceed 18 carbon atoms. The triarylphosphines are the preferred ligands, an example of which is triphenylphosphine.

(4) A concentration of the triorganophosphorus ligand in the reaction mixture which is sufficient to provide at least two, and preferably at least 5, moles of free ligand per mole of rhodium metal, over and above the ligand complexed with or tied to the rhodium atom.

(5) A temperature of from about 50° to about 145° C., preferably from about 60° to about 125° C.

(6) A total hydrogen and carbon monoxide pressure which is less than 450 pounds per square inch absolute (psia) preferably less than 350 psia.

(7) A maximum partial pressure exerted by carbon monoxide no greater than about 75 percent based on the total pressure of carbon monoxide and hydrogen, preferably less than 50 percent of this total gas pressure.

It is also known that, under hydroformylation conditions, some of the product aldehydes may condense to form by-product, high boiling aldehyde condensation products such as aldehyde dimers or trimers. Commonly-assigned U.S. Pat. No. 1,148,830, the entire disclosure of which is incorporated herein by reference thereto, discloses the use of these high boiling liquid aldehyde condensation products as a reaction solvent for the catalyst. In this process, solvent removal from the catalyst, which may cause catalyst losses, is unnecessary and, in fact, a liquid recycle containing the solvent high boiling aldehyde condensation products and catalyst is fed to the reaction zone from a product recovery zone. More specifically, as pointed out in said U.S. Pat. No. 4,148,830, some of the aldehyde product is involved in various reactions as depicted below using n-butyraldehyde as an illustration:

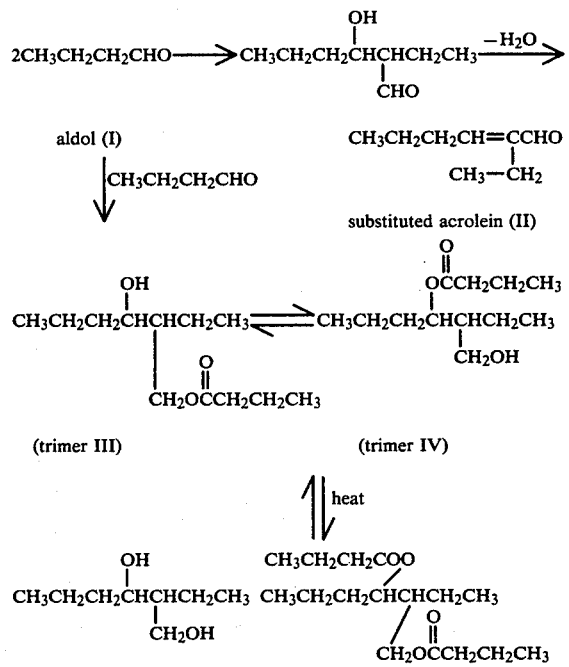

In addition, aldol I can undergo the following reaction:

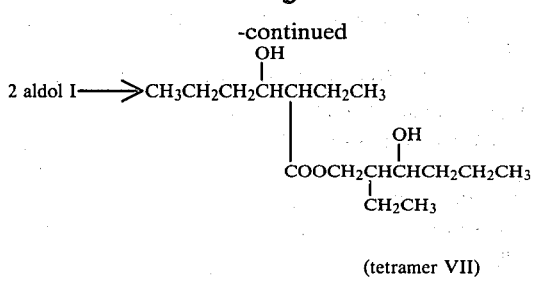

(tetramer VII)

The names in parentheses in the afore-illustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self-condensation of iso-butyraldehyde and a further range of compounds is formed by condensation of one molecule of normal butyraldehyde with one molecule of iso-butyraldehyde. Since a molecule of normal butyaldehyde can adolize by reaction with a molecule of iso-butyraldehyde in two different ways to form two different aldols VIII and IX, a total of four possible aldols can be produced by condensation reactions of a normal/iso mixture of butyraldehydes.

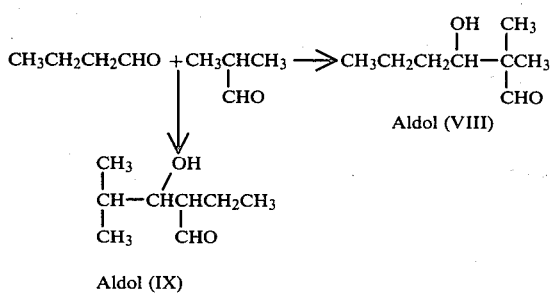

Aldol I can undergo further condensation with isobutyraldehyde to form a trimer isomeric with trimer III and aldols VIII and IX and the corresponding aldol X produced by self-condensation of two molecules of isobutyraldehyde can undergo further reactions with either normal or isobutyraldehyde to form corresponding isomeric trimers. These trimers can react further analogously to trimer III so that a complex mixture of condensation products is formed.

In addition commonly-assigned copending U.S. application Ser. No. 776,934, filed Mar. 11, 1977, now U.S. Pat. No. 4,247,486, the entire disclosure of which is incorporated herein by reference thereto, discloses a liquid phase hydroformylation reaction using a rhodium complex catalyst, wherein the aldehyde reaction products and some of their higher boiling condensation products are removed in vapor form from the catalyst containing liquid body (or solution) at the reaction temperature and pressure. The aldehyde reaction products and the condensation products are condensed out of the off gas from the reaction vessel in a product recovery zone and the unreacted starting materials (e.g., carbon monoxide, hydrogen and/or alpha-olefin) in the vapor phase from the product recovery zone are recycled to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self-condensation of the aldehyde product.

More specifically, according to said Ser. No. 776,934, a process for the production of an aldehyde containing from 3 to 6 carbon atoms is disclosed which comprises passing an alpha-olefin containing from 2 to 5 carbon atoms together with hydrogen and carbon monoxide at a prescribed temperature and pressure through a reaction zone containing the rhodium complex catalyst dissolved in a liquid body, continuously removing a vapor phase from the reaction zone, passing the vapor phase to a product separation zone, separating a liquid aldehyde containing product in the product separation zone by condensation from the gaseous unreacted starting materials, and recycling the gaseous unreacted starting materials from the product separation zone to the reaction zone.

It is also known in the prior art that even in the absence of intrinsic poisons there may be deactivation of rhodium hydroformylation catalysts under hydroformylation conditions. Copending, commonly-assigned U.S. patent application Ser. No. 762,336 filed Jan. 25, 1977, abandoned in favor of continuation U.S. application Ser. No. 151,293, the entire disclosure of which is incorporated herein by reference thereto, indicates that the deactivation of rhodium hydroformylation catalysts under hydroformylation conditions in the substantial absence of extrinsic poisons is due to the combination of the effects of temperature, phosphine ligand:rhodium mole ratio, and the partial pressures of hydrogen and carbon monoxide and is termed an intrinsic deactivation. It is further disclosed therein that this intrinsic deactivation can be reduced or substantially prevented by establishing and controlling and correlating the hydroformylation reaction conditions to a low temperature, low carbon monoxide partial pressure and high free triarylphosphine ligand:catalytically-active rhodium mole ratio. More specifically, this application discloses a rhodium-catalyzed hydroformylation process for producing aldehydes from alpha-olefins including the steps of reacting the olefin with hydrogen and carbon monoxide in the presence of a rhodium complex catalyst consisting essentially of rhodium complexed with carbon monoxide and a triarylphosphine, under certain defined reaction conditions, as follows:

(1) a temperature of from about 90° to about 130° C.;

(2) a total gas pressure of hydrogen, carbon monoxide and alpha-olefin of less than about 400 psia;

(3) a carbon monoxide partial pressure of less than about 55 psia;

(4) a hydrogen partial pressure of less than about 200 psia;

(5) at least about 100 moles of free triarylphosphine ligand for each mole of catalytically active rhodium metal present in the rhodium complex catalyst; and controlling and correlating the partial pressure of carbon monoxide, the temperature and the free triarylphosphine:catalytically active rhodium mole ratio to limit the rhodium complex catalyst deactivation to a maximum determined percent loss in activity per day, based on the initial activity of the fresh catalyst. By "catalytically active rhodium" is meant the rhodium metal in the rhodium complex catalyst which has not been deactivated. The amount of rhodium in the reaction zone which is catalytically active may be determined at any given time during the reaction by comparing the conversion rate to product based on such catalyst to the conversion rate obtained using fresh catalyst.

The manner in which the carbon monoxide partial pressure, temperature and free triarylphosphine:catalytically active rhodium mole ratio should be controlled and correlated to thus limit the deactivation of the catalyst is illustrated as follows.

As an example, for the triarylphosphine ligand triphenylphosphine, the specific relationship between these three parameters and catalyst stability is defined by the formula:

$$F = \frac{1000}{1 + e^y}$$

where
F = stability factor
e = Naperian log base (i.e., 2.718281828)
$y = K_1 + K_2T + K_3P + K_4 (L/Rh)$
T = reaction temperature (°C.)
P = partial pressure of CO (psia)
L/Rh = free triarylphosphine:catalytically active rhodium mole ratio
$K_1 = -8.1126$
$K_2 = 0.07919$
$K_3 = 0.0278$
$K_4 = -0.01155$ As pointed out in said Ser. No. 762,336, an olefin response factor must be employed to obtain the stability factor under actual hydroformylation conditions. Olefins generally enhance the stability of the catalyst and their effect on catalyst stability is more fully explained in said application. The above relationship is substantially the same for the triarylphosphines, except thst the constants $K_1$, $K_2$, $K_3$ and $K_4$ may be different. Those skilled in the art can determine the specific constants for other triarylphosphines with a minimum amount of experimentation as explained more fully in said application.

It is further taught in said Ser. No. 762,336 that it is generally desirable that the maximum loss of activity of the rhodium complex catalyst should be 0.75 percent per day, and highly advantageous results are achieved where the maximum rate of loss of catalyst activity is 0.3 percent per day, both being based upon the activity of the fresh catalyst. By the term "activity" is meant, for example, the amount of product produced expressed as gram-moles/liter-hour. Of course, any other standard technique can be employed to determine the relative activity of the catalyst at any given time. It should be understood, however, that the maximum acceptable rate of loss of catalyst activity would depend on many different factors, as pointed out above. The technique disclosed in said Ser. No. 762,336 provides a mechanism for obtaining any maximum rate of loss of catalyst activity by the control and correlation of the hydroformylation reaction conditions. Stated conversely, once a maximum acceptable rate of loss of catalyst activity is determined, the invention disclosed therein provides one skilled in the art with the tools of control and correlate the reaction conditions necessary to obtain catalyst stability. Therefore, the values given above for the maximum rate of loss of catalyst activity are provided merely to teach those skilled in the art how to practice that invention.

It has also been observed that the presence of an alkyldiarylphosphine (for example, propyldiphenylphosphine or ethyldiphenylphosphine) in the rhodium-catalyzed hydroformylation of the alpha-olefin propylene inhibits catalyst productivity; i.e., the rate at which the desired product aldehydes are formed. Specifically, the addition of small amounts of propyldiphenylphosphine or ethyldiphenylphosphine to rhodium hydroformylation solutions markedly reduced the rate of production of butyraldehydes from propylene, compared to the rate obtained in the absence of the alkyldiarylphosphines. This is shown by the data in Table A below:

TABLE A

| Entry | TPP[1] Amount (weight % of solution) | PDPP[2] or EDPP[3] Amount (weight % of solution) | PDPP or EDPP/ TPP Ratio | Aldehyde Production Rate (gram-moles/liter-hour) Observed | Predicted[4] | Comparative Rate of Production[5] |
|---|---|---|---|---|---|---|
| 1 | 4 | PDPP (0) | 0 | 1.03 | 1.02 | 100 |
| 2 | 1.89 | PDPP (2.0) | 1.05 | 0.36 | 1.06 | 34 |
| 3 | 3.74 | PDPP (0.67) | 0.18 | 0.53 | 1.02 | 53 |
| 4 | 4.06 | PDPP (1.33) | 0.33 | 0.79 | 1.87 | 42 |
| 5 | 3.61 | PDPP (1.33) | 0.37 | 1.51 | 3.51 | 43 |
| 6 | 4.0 | PDPP (0.05) | 0.013 | 0.62 | 1.02 | 60 |
| 7 | 9 | PDPP (1.0) | 0.11 | 0.60 | 0.69 | 87 |
| 8 | 6 | PDPP (1.0) | 0.17 | 0.54 | 0.63 | 86 |
| 9 | 9 | PDPP (3.0) | 0.33 | 0.54 | 0.72 | 75 |
| 10 | 6 | PDPP (3.0) | 0.5 | 0.47 | 0.68 | 68 |
| 11 | 9 | PDPP (1.0) | 0.11 | 0.55 | 0.69 | 80 |
| 12 | 6 | PDPP (1.0) | 0.17 | 0.58 | 0.63 | 92 |
| 13 | 9 | PDPP (3.0) | 0.33 | 0.39 | 0.72 | 54 |
| 14 | 6 | PDPP (3.0) | 0.5 | 0.52 | 0.68 | 77 |
| 15 | 9 | PDPP (0) | 0 | 0.80 | 0.60 | greater than 100 |
| 16 | 0 | PDPP (9) | ∞ | 0.273 | 0.60 | 46 |
| 17 | 0 | PDPP (4.5) | ∞ | 0.213 | 0.47 | 45 |
| 18 | 3.89 | EDPP (0.67) | | 0.42 | 1.02 | 42 |
| 19 | 3.69 | EDPP (0.67) | | 0.42 | 1.02 | 42 |
| 20 | 3.88 | EDPP (1.33) | | 0.33 | 1.02 | 33 |

TABLE A-continued

| Entry | TPP[1] Amount (weight % of solution) | PDPP[2] or EDPP[3] Amount (weight % of solution) | PDPP or EDPP/ TPP Ratio | Aldehyde Production Rate (gram-moles/ liter-hour) Observed | Predicted[4] | Comparative Rate of Production[5] |
|---|---|---|---|---|---|---|
| 21 | 6.95 | EDPP (0.67) | | 0.32 | 0.82 | 39 |
| 22 | 6.85 | EDPP (1.33) | | 0.24 | 0.82 | 29 |

[1] TPP = triphenylphosphine
[2] PDPP = propyldiphenylphosphine
[3] EDPP = ethyldiphenylphosphine
[4] Predicted rate determined from a kinetic rate expression
[5] Comparative Rate of Production = $\frac{\text{observed rate}}{\text{predicted rate for same conditions with same total phosphine but all TPP}} \times 100$ Although the presence of alkyldiarylphosphines in rhodium-catalyzed hydroformylation processes reduces the catalyst productivity, the stability of such rhodium complex catalysts can be enhanced by providing an alkyldiarylphosphine in the reaction medium and copending, commonly assigned U.S. application Ser. No. 762,335 filed Jan. 25, 1977 abandoned in favor of continuation U.S. application Ser. No. 140,830, now U.S. Pat. No. 4,260,828, the entire disclosure of which is incorporated herein by reference thereto, teaches that the reaction conditions can be adjusted to be more severe in order to regain this apparent loss of catalyst productivity while retaining the enhanced catalyst stability.

The invention in said Ser. No. 762,335 relates to an improvement in a rhodium-catalyzed process for hydroformylating an alpha-olefin to produce aldehydes having one more carbon atom than the alpha-olefin, which process includes the steps of reacting the alpha-olefin with hydrogen and carbon monoxide, in a liquid reaction medium which contains a soluble rhodium complex catalyst consisting essentially of rhodium complexed with carbon monoxide and a triarylphosphine ligand, wherein the improvement comprises improving the stability of the catalyst by providing in the liquid reaction medium containing the catalyst an amount of an alkyldiarylphosphine ligand; and controlling the hydroformylation reaction conditions as follows:

(1) a temperature of from about 100° to about 140° C.;

(2) a total gas pressure of hydrogen, carbon monoxide and alpha-olefin of less than about 450 psia;

(3) a carbon monoxide partial pressure of less than about 55 psia;

(4) a hydrogen partial pressure of less than about 200 psia;

(5) at least about 75 moles of total free phosphine ligand for each mole of catalytically-active rhodium metal present in the rhodium complex catalyst.

Said Ser. No. 762,335 further teaches that generally, the amount of the alkyldiarylphosphine ligand present in the liquid reaction medium can be from about 0.1 to about 20 percent by weight, based upon the total weight of the liquid reaction medium. When a triarylphosphine ligand is employed in the hydroformylation of an alpha-olefin, some alkyldiarylphosphine is produced in situ, the "alkyl" group thereof being derived from the alpha-olefin undergoing hydroformylation and the "aryl" groups thereof being the same as the aryl of the triarylphosphine. Therefore, it may not be necessary to add additional alkyldiarylphosphine to the reaction medium to provide a sufficient amount of the same therein. The particular amount of alkyldiarylphospine in the reaction medium will depend on several factors such as the particular alpha-olefin reacted, the reaction conditions, the desired rate of reaction, etc.

Said Ser. No, 762,335 further discloses that when an alkyldiarylphosphine ligand is present in a liquid reaction medium containing a rhodium complex catalyst consisting essentially of rhodium complexed with carbon monoxide and a triarylphosphine ligand, the resulting rhodium complex catalyst consists essentially of rhodium complexed with carbon monoxide and either one or both of the triarylphosphine ligand and the alkyldiarylphosphine ligand and that the terminology "consists essentially of" is not meant to exclude, but rather to include, hydrogen complexed with the rhodium, in addition to carbon monoxide and triarylphosphine and-/or alkyldiarylphosphine. However, this language is meant to exclude other materials in amounts which poison or deactivate the catalyst.

Said Ser. No. 762,335 goes on to disclose that particularly advantageous results are achieved when the amount of total free phosphine ligand in the liquid reaction medium is at least about 100 moles per mole of catalytically-active rhodium metal present in the rhodium complex catalyst. The upper limit of the amount of total free phosphine liqand is not particularly critical and would be dictated largely by commercial and economic considerations. Higher mole ratios of total free phosphine: catalytically-active rhodium metal favor the stability of the catalyst. By "total free phosphine" is meant the triarylphosphine and/or alkyldiarylphosphine that is not tied to or complexed with the rhodium atom in the active complex catalyst. The theory of how such ligands complex with the rhodium is given in said U.S. Pat. No. 3,527, 809.

Despite the obvious advantages of the inventions discussed above the continued build-up of alkyl substituted phosphine over a period of time in a continuous hydroformylation reaction of alpha-olefins to produce aldehydes rich in the normal isomer eventually leads to an unacceptable decrease in the rate of reaction and activity of the rhodium complex catalyst due to the affinity of said alkyl substituted phosphine for the rhodium catalyst. Thus it would be clearly beneficial to the state of the art if one could selectively remove undesirable alkyl substituted phosphine from the liquid reaction medium of the hydroformylation reaction without adversely affecting the beneficial triarylphosphine and complex catalyst present therein.

However, even after enhancing the activity of the rhodium complex catalyst by removal of alkyl substituted phosphine from the hydroformylation reaction medium, eventually the rhodium complex catalyst will become spent (that is to say such enhancing procedures cannot be repeated indefinitely since eventually the activity of the catalyst will have decreased to such a point that it is not longer economically desirable to operate the hydroformylation process) and the catalyst will have to be replaced. Moreover, improper procedures and/or contaminates, and the like at the initial start-up of a hydroformylation process could result in an early undesirabl hydroformylation medium that must also be replaced.

Upon such occurrences it becomes important to recover the rhodium values of the complex catalyst due to the inordinately high cost of rhodium. Such recovery methods will obviously entail the removal and/or destruction of the organic compounds of the hydroformylation composition, and such poses the problem of what to do with the large excess of triarylphosphine employed or the small amount of such triarylphosphine that may remain after classical removal mens, such as distillation. Accordingly, it would clearly be beneficial to the state of the art if such large or small amounts of triarylphosphine could be easily removed from such compositions or concentrates thereof, and ecologically disposed of without unduly and adversely affecting the environment.

SUMMARY OF THE INVENTION

It has now been discovered that triorganophosphine selected from the class consisting of alkyl subtituted phosphine and triarylphosphine can be easily removed from a rhodium containing composition or rhodium containing concentration thereof.

Thus it is an object of this invention to provide a process for removing triorganophosphine selected from the class consisting of alkyl substituted phosphine and triarylphosphine from a rhodium containing composition or rhodium containing concentrate of said composition. It is another object of this invention to provide a process for selectively removing alkyl substituted phosphine from a liquid rhodium containing composition which also contains a rhodium complex catalyst and triarylphosphine. It is a further object of this invention to provide a method for rejuvenating the activity of a rhodium complex catalyst of a hydroformylation reaction by removing alkyl substituted phosphine from the liquid reaction medium of said hydroformylation reaction. Other objects and advantages of this invention will become readily apparent from the following description and appended claims.

Accordingly, the generic aspect of this invention can be described as a process for removing triorganophosphine selected from the class consisting of triarylphosphine and alkyl substituted phosphine of the formula

(I)

wherein R is an alkyl radical, R' is an alkyl or aryl radical and R" is an aryl radical from a liquid rhodium containing composition or a rhodium containing concentrate of said composition, said process comprising (1) mixing (a) a rhodium containing composition comprising a rhodium complex hydroformylation catalyst, triarylphosphine and alkyl substituted phosphine of formula (I) above, or (b) a rhodium containing concentrate of said composition, with an $\alpha,\beta$-unsaturated compound selected from the group consisting of compounds having the formula

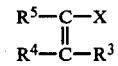

wherein X is a radical selected from the group consisting of

—CN, —Cl, —Br, —I, —NO$_2$, and —OR$^7$; R$^6$ is a radical selected from the group consisting of hydrogen, alkyl, aryl, hydroxy, alkoxy, amino and halogen; R$^7$ is an alkyl or aryl radical; and R$^3$, R$^4$ and R$^5$ are each individually radicals selected from the group consisting of hydrogen, alkyl, aryl, X radicals as defined above and —CH$_2$X radicals wherein X is the same as defined above; and wherein R$^4$ and R$^5$ taken together can form an alkylene group having from 2 to 8 carbon atoms; and anhydrides of the carboxylic acids of said $\alpha,\beta$-unsaturated formula compounds;

(2) allowing an aqueous mixture of said step (1) to settle into two distinct liquid phases, and (3) separating the aqueous phase which contains the solubilized reaction products of the alkyl substituted phosphine and/or triarylphosphine present in said composition or concentrate with said $\alpha,\beta$-unsaturated compound from the non-aqueous liquid phase resulting from said steps (1) and (2); and wherein the molar ratio of the amount of said $\alpha,\beta$-unsaturated compound employed to the total amount of the alkyl substituted and/or triarylphosphine present in said composition or concentrate is at least 0.1 to 1; and wherein the amount of water employed is at least sufficient to solubilize that amount of the reaction products of said phosphines with $\alpha,\beta$-unsaturated compound resulting from said steps (1) and (2).

DESCRIPTION OF THE PREFERRED EMBODIMENTS

The liquid rhodium containing composition from which the triorganophosphines are removed by the present invention can be prepared in any manner and may contain, if desired, additional ingredients, such as solvents for the rhodium complex hydroformylation catalyst, which do not essentially interfere with the course of the novel process of this invention. More preferably, said liquid rhodium containing composition is derived from a hydroformylation process for the production of aldehydes from an alpha olefin. As pointed out by the above prior art, methods for hydroformylating olefins to produce aldehydes with a rhodium complex catalyst in the presence of triarylphosphine are well known in the art and such methods can result in the in situ formation of an alkyl substituted phosphine of Formula (I) above, the "alkyl" group thereof being derived primarily from the olefin undergoing hydroformylation and the "aryl" group thereof being the same as the aryl radical of the triarylphosphine employed. Of course, it is to be understood that while the alkyl substituted phosphine present in the liquid rhodium containing compositoin of this invention is primarily that derived from its in situ formation as explained above, the definition of the present invention is not meant to exclude, but rather includes the possible presence of any deliberatley added, if such was desired, alkyl substituted phosphine, such as that discussed and explained in U.S. application Ser. No. 762,335 above.

Thus, it should be clear that the particular hydroformylation process for producing aldehydes from an olefin from which the liquid rhodium containing composition employed in the present invention may be derived, as well as the reaction conditions and ingredients of said hydroformylation process are not critical features of the present invention, since such serves only as a means for furnishing the liquid rhodium containing composition employed as a starting material of the present invention. In general, however, the preferred liquid rhodium containing compositions employed in the present invention are those hydroformylation reaction mediums derived from the preferred operational features taught in U.S. Pat. No. 3,527,809 and U.S. Application Ser. Nos. 762,335 and 776,934 discussed above.

Accordingly, the preferred liquid rhodium containing composition employed in this invention can be more specifically defined as a liquid rhodium containing composition comprising (a) a rhodium complex catalyst consisting essentially of rhodium complexed with carbon monoxide, triarylphosphine and/or alkyl substituted phosphine of the formula

wherein R, R' and R" are the same as defined above, (b) free triarylphosphine, and (c) free alkyl substituted phosphine of the formula

wherein R, R' and R" are the same as defined above.

Therefore, the rhodium complex catalyst present in the liquid rhodium containing composition of this invention will generally and preferably be one that is formed under the conditions of a hydroformylation process in the liquid reaction medium of said process. For example, as seen by the preferred operational features taught in U.S. Pat. No. 3,527,809 and U.S. Application Ser. Nos. 762,335 and 776,934 discussed above, the preferred hydroformylation reaction mediums employ a rhodium complex catalyst consisting essentially of carbon monoxide and a triarylphosphine ligand and free triarylphosphine. As the hydroformylation reaction continues alkyl substituted phosphine of Formula (I) above is formed in situ, the amount of which continues to build up over the period of time that the continuous hydroformylation process is operational and said alkyl substituted phosphine ligand having a greater affinity for rhodium than triarylphosphine also ties or binds itself to the rhodium thereby resulting in a rhodium complex catalyst consisting essentially of rhodium complexed with carbon monoxide, triarylphosphine ligand and/or said alkyl substituted phosphine ligand (i.e. either one or both of said triarylphosphine ligand and said alkyl substituted phosphine ligand) in the liqquid reaction medium of said process, which medium also serves as the preferred liquid rhodium containing composition of this invention.

Moveover, it is to be understood that, while the liquid rhodium containing composition employed in this invention contains a rhodium complex catalyst consisting essentially of rhodium complexed with carbon monoxide, triarylphosphine ligand and/or alkyl substituted phosphine ligand of formul (I) above, the terminology "consisting essentially of" is not meant to exclude, but rather include, hydrogen complexed with the rhodium in addition to carbon monoxide, triarylphosphine and/or alkyl substituted phosphine, said hydrogen and carbon monoxide of course being derived from the hydrogen and carbon monoxide gases which are an integral part of any hydroformylation process. It is not intended to limit the present invention by the above explanation as to which phosphine (or relative amount thereof) is tied to or complexed with the rhodium, nor as to the relative proportions of which phosphine is free, although it has been determined that, as between triphenylphosphine and propyldiphenylphosphine, the rhodium exhibits a preference for the latter over the former as to which it is tied or bound to. Clearly it is sufficient for the purposes of this invention to simply provide a method for removing said alkyl substituted phosphine and triarylphosphine from the liquid rhodium containing composition.

As pointed out in the above discussed prior art, the rhodium complex catalyst employed in hydroformylation reactions may be formed by methods known in the art. For example, a preformed stable crystalline solid of rhodium hydridocarbonyl-tris (triphenylphosphine), may be introduced into the reaction medium of a hydroformylation process. Such a material may be formed for example, by a method disclosed in Brown et al., *Journal of the Chemical Society*, 1970, pages 2753–2764. Alternatively, and this is preferred, the rhodium complex catlayst present in the liqquid rhodium containing composition of this invention is derived from a rhodium catalyst precursor such as rhodium carbonyl triphenylphosphine acetylacetonate, $Rh_2O_3$, $Rh_4(CO)_{12}$, $Rh_6(CO)_{16}$, $Rh(NO_3)_3$ or rhodium dicarbonyl acetylacetonate, and the like, which have been introduced into the reaction medium of a hydroformylation process and form the rhodium complex catalyst consisting essentially of carbon monoxide and triarylphosphine of said hydroformylation process which in turn serves as the basis the in situ formation of the rhodium complex catalyst present in the liquid rhodium containing composition of this invention. In either event, an active rhodium complex catalyst is formed in the hydroformylation reaction medium under the conditions of hydroformylation, wherein said alkyl substituted phosphine is formed in situ or is desired, is added to the reaction medium or both. Of course, it is also possible to preform a rhodium complex catalyst which contains both triarylphosphine and said alkyl substituted phosphine complexed with the rhodium if desired.

The triarylphosphine, both complexed with rhodium and free, present in the liquid rhodium containing composition of this invention can of course be any triarylphosphine suitable for use in any hydroformylation reaction such as those triarylphosphines and reactions taught by the prior art discussed above. Illustrative triarylphosphine ligands are triphenylphosphine, trinaphthylphosphine, tritolylphosphine, tri(p-biphenyl) phosphine, tri-(p-methoxyphenyl) phosphine, p-(N, N-dimethylamino)phenyl diphenylphosphine, and the like. Triphenylphosphine is presently the preferred triarylphosphine ligand.

The alkyl substituted phosphine, both complexed with rhodium and free, present in the liquid rhodium containing composition of this invention can be any phosphine that is more nucleophilic (basic) that the triarylphosphine in said composition. For example, propyldiphenylphosphine is more basic (pKa=about 4.5 to 5.5) than triphenylphosphine (pKa=2.73). Illustrative examples of such alkyl substituted phosphines include those encompassed by Formula (I) above. Moreover, as explained above, such alkyl substituted phosphines are normally derived from the particular olefin that is hydroformylated and the particular triarylphosphine employed in said hydroformylation process. For example, the hydroformylation of propylene by the preferred procedure described in U.S. Application Ser. No. 776,934 leads to the in situ formation of propyldiphenylphosphine as well as some detectable butyldiphenyl phosphine. Dialkylarylphosphines, which may be present as a result of in situ formation or deliberate addition are more nucleophilic than the triarylphosphine and can also be removed by the process of this invention.

Accordingly, the alkyl radical of said alkyl substituted phosphine may be any alkyl radical containing 2 to 20, preferably 2 to 10, carbon atoms. They may be straight or branched-chain and may contain groups or substituents which do not essentially interfere with the course of the process of this invention, such as hydroxyl and alkoxy radicals, and the like. Illustrative of such alkyl radicals include ethyl, propyl, isopropyl, butyl, pentyl, hexyl, heptyl, octyl, decyl, dodecyl, octadecyl, 2-ethyl-hexyl, eicosyl, 3-phenyl-propyl, 3-hydroxypropyl, 4-hydroxyhexyl, 4-hydroxyoctyl, 2-ethoxyethyl, 2-methoxyethyl, 3-ethoxypropyl, and the like.

Moreover, since it is generally preferred to hydroformylate alpha-olefins containing 2 to 5 carbon atoms the more preferred alkyl radicals of said alkyl substituted phosphines are ethyl, propyl, butyl and pentyl. Likewise, the aryl radical of said alkyl substituted phosphines may correspond to the aryl group of the triarylphosphine ligand employed in the hydroformylation processes as discussed above, the preferred aryl radical being a phenyl radical derived from triphenylphosphine. The most preferred alkyl substituted phosphines are ethyldiphenylphosphine, propyldiphenylphosphine and butyldiphenylphosphine, especially propyldiphenylphosphine. Note, however, that it is not applicants' intention to be bound by any precise discussion or explanation of how said alkyl substituted phosphines are formed in situ, it being sufficient for the purpose of this invention to simply point out that their in situ formation is possible and that such alkyl substituted phosphines can be selectively removed when present in the liquid rhodium containing composition employed in this invention.

The various amounts of rhodium complex catalyst, triarylphosphine and said alkyl substituted phosphine contained in the liquid rhodium containing composition of this invention are not critical since the subject invention is directed to a process for removing all or any portion of said alkyl substituted phosphine and triarylphosphine present in a liquid rhodium containing composition which also contains any amount of said rhodium complex catalyst. Moreover, since the preferred liquid rhodium containing compositions of this invention correspond to the liquid reaction medium of any hydroformylation reaction such as discussed above, the amounts of said rhodium complex catlyst, triarylphosphine and alkyl substituted phosphine will preferably be those amounts employed and/or obtained in situ in the liquid reaction medium of said hydroformylation reaction from which it is desired to remove said alkyl substituted phosphine and triarylphosphine. Accordingly, the generic and preferred amounts of such ingredients initially employed in a hydroformulation reaction are well known in the art and are merely dependent upon the particular hydroformylation reaction employed. It should also be clear that the amount of alkyl substituted phosphine present herein will also preferably be merely dependent upon the amount of alkyl substituted phosphine that has formed in situ and accumulated as a result of the particular hydroformylation process employed over the time period that said process has been operational. Thus, since it is generally desired to employ the process of this invention to rejuvenate the activity of the rhodium complex catalyst of a continuous hydroformylation reaction, in general the amount of the alkyl substituted phosphine ligand present in the liquid rhodium containing composition employable in this invention may range from about 0.1 to about 20 percent by weight based on the total weight of the liquid rhodium containing composition, while the amount of triarylphosphine ligand present in the liquid rhodium containing composition employable in this invention may vary from about 0.5 percent to about 40 percent or higher by weight, based on the total weight of the liquid rhodium containing composition. Moreover, in the preferred hydroformylation reactions particularly advantageous results are achieved when the amount of total free phosphine ligand (i.e. that amount that is not complexed with the rhodium atom in the active complex catalyst) in the liquid reaction medium is at least about 100 moles per mole of catalytically-active rhodium metal present in the rhodium complex catalyst. The upper limit of the amount of total free phosphine ligand is not particularly critical and would be dictated largely by commercial and economic considerations. Likewise the amount of rhodium complex hydroformylation catalyst present in the liquid rhodium containing composition of this invention will generally be at least that minimum amount (catalytic amount) which is necessary to catalyze the particular hydroformylation reaction from which the preferred liquid rhodium containing composition of this invention is derived. Generally, the rhodium concentration in the liquid composition may range from about 25 ppm to about 1200 ppm, and preferably about 50 ppm is about 400 ppm, of catalytically active rhodium calculated as the free metal. It is further preferred that the liquid rhodium containing composition of this invention contain at least one percent by weight of alkyl substituted phosphine based on the total weight of the liquid rhodium containing composition while the amount of triarylphosphine present is at least twice as much as that of said alkyl substituted phosphine.

It is of course, also to be understood that since the rhodium complex catalyst of hydroformylation reactions are soluble complexes, as are the rhodium complex catalysts defined herein, and since said hydroformylation reactions are normally conducted in the presence of a solvent for such catalyst, then the liquid rhodium containing compositions employed in this invention can also encompass the presence of such solvents for said catalysts in the same amounts that such solvents are present in the liquid reaction medium of said hydroformylation reactions. Such solvents are well known in the art and encompass those described in U.S.P. at No. 3,527,809 and more preferably the higher boiling liquid aldehyde condensation products which are described more fully as are methods for their preparation in U.S. Application Ser. No. 776,934 and U.S.P. at No.

4,148,830 as discussed above. Such condensation products can be preformed or produced in situ during hydroformylation and include the complex mixture of high boiling liquid products which result from the condensation reactions of some of the aldehyde products of the hydroformylation process as discussed above. The rhodium complex catalyst of the initial hydroformylation as well as that formed in situ is not only soluble in said condensation products but also exhibit excellent stability over extended periods of continuous hydroformylation. In a preferred form of hydroformylation the higher boiling liquid aldehyde condensation products to be used as solvents are preformed prior to introduction into the reaction zone and the start up of the hydroformylation process. Accordingly, the amount of solvent present in the liquid rhodium containing composition of this invention is not critical to the subject invention and will preferably be those amounts employed and/or maintained in situ in the liquid reaction medium of said hydroformylation reaction. Thus, in general, the amount of solvent when present in the liquid composition of this invention may range from about 10 to 95 parts by weight based on the total weight of the liquid composition. Of course, it should be also understood that since the liquid rhodium containing composition of this inventoin is preferably all or any portion of the liquid reaction medium of a hydroformylation reaction, then said liquid composition can also encompass the possible presence of minor amounts of the starting materials, by-products, and/or aldehyde products of such hydroformylation reactions.

While one aspect of this invention is preferably directed to selectively removing all or any portion of said alkyl substituted phosphine from said liquid rhodium containing composition, it is to be understood that this invention can also be employed to remove all or any portion of said triarylphosphine from said liquid rhodium containing composition if desired. For example, the subject invention can also be employed to remove the large amounts of free triarylphosphine found in spent or contaminated rhodium catalyzed hydroformylation mediums as discussed above in order to facilitate recovery of the rhodium values of said mediums if such is desired.

Moreover, this invention can further be employed to remove said alkyl substituted phosphine and/or triarylphosphine from any rhodium containing concentrate derived from the liquid rhodium containing compositions employable in this invention. The term "rhodium containing concentrate" as employed herein encompasses any distillation residue containing rhodium and free triarylphosphine obtained upon concentrating the rhodium containing compositions employable in this invention which have been defined herein above. Accordingly said rhodium containing concentrates may be derived by distilling said rhodium containing compositions in any manner such that the distillation residue or concentrate so obtained contains rhodium and at least some free triarylphosphine. Thus the particular distillation procedure for producing the rhodium containing concentrates employable in this invention is merely dependent upon the concentrate that may be desired. Accordingly, the rhodium containing concentrates employable in this invention encompass any distillation residue of the rhodium containing compositions employable in this invention from which any amount of one or more of the above defined ingredients of said rhodium containing compositions have been removed via distillation, provided that said concentrates still contain at least some rhodium and some free triarylphosphine.

For instance, the rhodium containing concentrates employable in this invention can be those rhodium complex concentrates that have been produced by a process which comprises concentrating a spent hydroformylation reaction medium, i.e. a liquid rhodium containing composition as defined herein above which contains a partially deactivated rhodium complex catalyst and free triarylphosphine, by means of distillation at temperatures of about 20° C. to about 350° C. and at pressures of about 1000 mm Hg. to about $1 \times 10^{-6}$ mm Hg. to obtain a distillation residue containing a major amount of the rhodium of said catalyst and free triarylphosphine and which has been concentrated to about 0.1 to about 30 percent by weight of said spent hydroformylation reaction medium.

The preferred rhodium containing concentrates are brownish, highly viscous rhodium complex mediums consisting of rhodium and minor amounts of free triarylphosphine (generally less than 10 percent by weight based on the total weight of the concentrate), the remainder consisting essentially of highly boiling aldehyde condensation products and phosphine oxides, said condensation products and oxides having been derived in situ during the hydroformylation process from whence the spent hydroformylation reaction medium is obtained The distillation procedure which may be employed to prepare such preferred rhodium containing concentrates can be found more fully discussed in U.S. Application Ser. No. 58,123 filed July 16, 1979, now abandoned, the entire disclosure of which is incorporated herein by reference thereto. For instance, said application Ser. No. 58,123 discloses preparing rhodium containing concentrates that have been concentrated to about 0.1 to about 30 percent by weight of said spent hydroformylation reaction medium. More preferably the spent hydroformylation reaction medium is distilled to form a rhodium complex concentrate which has been concentrated to from about 1 to about 10 percent by weight and most preferably to from about 2 to about 6 percent by weight of said spent medium.

Such a distillation procedure preferably takes place in two stages, the first stage being conducted at temperatures of about 20° to 250° C., preferably from 20° to 190° C., and pressures of about 1000 to about 0.1 mm Hg., preferably about 150 to 0.5 mm Hg., which may effect up to about a threefold concentration of the spent hydroformylation reaction medium; the second stage of the distillation being conducted at temperatures of about 25° to 350° C., preferably from about 150° to about 300° C., and pressures of about 100 to $1 \times 10^{-6}$ mm Hg., preferably about 20 to 0.1 mm Hg., so as to further concentrate the bottom or residue product of the first stage to the finally desired rhodium complex concentrate which may contain from about 1000 to about 50,000 ppm, more preferably from about 2000 to about 15,000 ppm, and most preferably from about 4,000 to 12,000 ppm, of rhodium calculated as free metal.

The first distillation stage is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) components. Of course it is obvious that the most volatile components (e.g. the aldehyde products) so removed may be recovered from said distillate stream in any conventional manner or discarded as desired.

The second distillation stage involves taking the liquid residue or bottoms of said first distillation stage containing the partially deactivated rhodium complex catalyst and less volatile components, such as the solvent and phosphine ligands, of the spent hydroformylation reaction medium and subjecting it to further distillation at the reduced pressures given above so as to distill off and remove said remaining high boiling volatile materials. The rhodium containing complex concentrate employable in this invention is thus recovered as the distillation residue of said second stage distillation and contains a major amount of the rhodium of said partially deactivated catalyst (i.e. more than 50 percent by weight, preferably more than 90 percent by weight, of the total amount of rhodium of said catalyst). For obvious economic reasons it is most desirable that the rhodium complex concentrate contain essentially (i.e. greater than 97 percent by weight) all of the rhodium of said partially deactivated catalyst.

The distillation of each separation stage can be carreid out by using any suitable distillation system and can take place on a continuous and/or discontinuous (batch) basis. However, care should be taken to avoid overheating the rhodium complex. It is also important to maintain a high vacuum in the second distillation stage so that the temperature required for concentration can be minimized. Thus the distillation is preferably carried out at the lowest temperature and shortest residence time required to achieve the desired rhodium concentration. Because the components of the spent hydroformylation reaction mediums which are to be distilled can vary, both in terms of their nature and concentrations, as well as from hydroformylation process to hydroformylation process, it is apparent that no specific residence time can be arbitrarily given as either a maximum or minimum in order to practice said distillation. Accordingly, it is preferred to employ a thin-film evaporator, such as a wiped-film evaporator, since in such systems residence times at elevated temperatures of less than 10 minutes would be suitable in most instances, and preferably such residence times will be less than about three minutes, whereas in a kettle-type batch distillation the residence time for the second stage of distillation can be hours. However, batch systems are readily suitable for the first stage of distillation, since such is concerned with only removing the most volatile (lower boiling) components of the spent medium and thus the distillation can be carried out at rather mild temperatures and at much higher pressures than those pressures employed in the second distillation stage. In general, it is preferred to carry out both distillation stages in a thin-film evaporator, especially a wiped-film evaporator. Such evaporators are well known in the art and thus need not be further discussed herein.

As pointed out above a broad range of $\alpha,\beta$-unsaturated compounds can be employed herein to remove said triorganophosphines from said rhodium containing compositions or rhodium containing concentrates thereof. Such $\alpha,\beta$-unsaturated compounds include those containing from 2 to 18 carbon atoms, preferably from 3 to 10 carbon atoms, selected from the group consisting of compounds of the formula

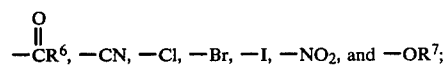

wherein X is an electron withdrawing radical selected from the group consisting of

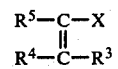

$-CR^6$, $-CN$, $-Cl$, $-Br$, $-I$, $-NO_2$, and $-OR^7$;

and $-OR^7$; $R^6$ is a radical selected from the group consisting of H, alkyl, aryl, hydroxy, alkoxy, amino and halogen; $R^7$ is an alkyl or aryl radical, and $R^3$, $R^4$ and $R^5$ are each individually selected from the group consisting of hydrogen, alkyl, aryl, -X radicals as defined above and $-CH_2X$ radicals wherein X is the same as defined above; and wherein $R^4$ and $R^5$ taken together can form an alkylene group having from 2 to 8 carbon atoms; and anhydrides of the carboxylic acids of said formula compounds. Of course it is understood that mixtures of two or more $\alpha,\beta$-unsaturated compounds can be employed if desired. The preferred $\alpha,\beta$-unsaturated compounds are those containing more than one electron withdrawing radical and wherein at least one of said $R^3$ and $R^4$ groups is hydrogen, since they are the most reactive towards said triorganophosphines, the more preferred electron withdrawing radical being $-COOH$.

Illustrative examples of such $\alpha,\beta$-unsaturated compounds include maleic acid, maleic anhydride, acrylic acid, itaconic acid, crotonic acid, ethyl acrylate, acrylonitrile, acrolein, crotonaldehyde, methacrolein, ethylpropyl-acrolein, cyclohex-1-ene carboxylic acid, acrylic acid chloride, ethylvinylether, fumaric acid, and the like. The most preferred $\alpha,\beta$-unsaturated compounds are maleic acid and maleic anhydride, especially maleic acid.

The process of this invention comprises mixing the rhodium containing composition or rhodium containing concentrate thereof, as defined above, with the $\alpha,\beta$-unsaturated compound, allowing an aqueous mixture thereof to settle into two distinct liquid phases and separating the aqueous (bottom) phase which contains the solubilized products of the alkyl substituted phosphine and/or triarylphosphine from the other liquid (i.e. nonaqueous, top) phase containing the remainder of the starting rhodium containing composition or concentrate thereof.

The process of this invention may be described as one in which the phosphine compounds of the rhodium containing composition and/or rhodium containing concentrate thereof react quickly with the $\alpha,\beta$-unsaturated compound to form phosphorous ylides which in the presence of the water hydrolyze to form a water soluble phosphonium salt as seen by the following illustrated general reaction.

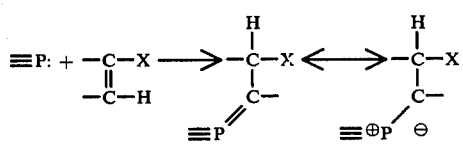

Furthermore, while it is not intended to limit the present invention by the above explanation as to the precise order of reaction involved it has been found that the alkyl substituted phosphines are more reactive towards the $\alpha,\beta$-unsaturated compound than triarylphosphine and thus provide the basis for selective removal of the alkyl substituted phosphine from the rhodium containing composition or concentrate thereof in the form of water solubilized reaction products of said alkyl substituted phosphines with said $\alpha,\beta$-unsaturated compound. Furthermore, it is not intended to be bound by any discussion of the particular structure of the solubilized reaction product, although it is believed to be a phosphonium salt, since it is sufficient for the purposes of the present invention to simply provide a means for removing the alkyl substituted phosphine and/or triarylphosphine. Nor is it intended to limit the present invention by any discussion as to the order of removal of the phosphine complexed with the rhodium catalyst and the free phosphine, since it is sufficient for the purpose of this invention to simply understand that all or any portion of the free phosphine can be removed from the rhodium containing compositions or concentrates thereof by the process of this invention.

The reaction of the process of this invention is exothermic and can be carried out at any suitable temperature. Moreover, the process can be carried out at sub, atmospheric, or elevated pressures, as desired. In general, the temperature may range from about 0° C. to about 150° C. Temperatures of 100° C. and above, of course, require elevated pressures. Preferably, the process is performed at about atmospheric pressure and at less than 100° C. the more preferred temperature being from about 25° C. to about 80° C. It is important to thoroughly mix the reactants involved, and such can be effected by any conventional means such as stirring and the like. The general reaction is quite rapid and will normally be completed within an hour and more preferably within one-half hour depending on the reactants, temperature and efficiency of mixing involved.

In general, one mole of triorganophosphine compound will react with one mole of $\alpha,\beta$-unsaturated compound. Accordingly the molar ratio of the amount of said $\alpha,\beta$-unsaturated compound employed in relation to the total amount of triorganophosphine desired to be removed from the starting rhodium containing composition and/or rhodium containing concentrate thereof is at least 0.1 to 1. The upper limit of the amount of said $\alpha,\beta$-unsaturated compound is not critical. Thus the use of 0.1 to about 100 mole equivalents, preferably about 0.1 to about 25 mole equivalents of said $\alpha,\beta$-unsaturated compound per mole equivalent of the total amount of said triorganophosphine desired to be removed should be satisfactory in most instances. Further, when the process of this invention is designed for the selective removal of alkyl-substituted phosphine and not triarylphosphine from the rhodium-containing composition and/or concentrate thereof, some triarylphosphine may be and undoubtedly is also removed from the rhodium-containing starting material in the same manner as described above (i.e., as a solubilized reaction product with the $\alpha,\beta$-unsaturated compound) and thus the molar ratio of the amount of said $\alpha,\beta$-unsaturated compound employed in relation to the total amount of said triarylphosphine present in said starting rhodium containing composition and/or concentrate thereof should be less than 1 to 1 to ensure retention of the triarylphosphine in the starting composition and/or concentrate. This it is preferred to employ about one to about five mole equivalents of said $\alpha,\beta$-unsaturated compound per mole equivalents of alkyl-substituted phosphine when desiring to selectively remove said alkyl-substituted phosphine to ensure sufficient removal of said alkyl-substituted phosphine without incurring large triarylphosphine losses. On the other hand, when it is desired to remove all detectable triarylphosphine from said starting rhodium-containing compositions and/or concentrate thereof, the process also removes alkyl-substituted phosphine, if present, in the same manner as described above (i.e., as a water-solubilized reaction product with the $\alpha,\beta$-unsaturated compound). In such instances it is thus preferred that the molar ratio of said $\alpha,\beta$-unsaturated compound in relation to the total amount of said triarylphosphine and said alkyl-substituted phosphine present in said starting rhodium containing compositions and/or concentrates thereof be at least 1 to 1 and preferably from 1 to 25:1.

While it is normally preferred to conduct the mixing of the rhodium containing composition or rhodium containing concentrate thereof with the $\alpha,\beta$-unsaturated compound in the present of water, if desired, very viscous rhodium containing concentrates, such as the preferred concentrates described above, can be mixed with the $\alpha,\beta$-unsaturated compound in the absence of water and the aqueous mixture formed by a later addition of water. However, even in the case of very viscous concentrates, it is more convenient to form a solubilized solution of the very viscous concentrate and then mix said concentrate solution with the $\alpha,\beta$-unsaturated compound in the presence of water. Suitable solvents for said viscous concentrates include alcohols, e.g., butanol, and the like, aldehyde condensation products, e.g., Texanol ®, and the like. Of course, it is obvious that any amount of solvent may be employed. In general, amounts of solvent ranging from about 0.5 to about 50 parts by volume per volume part of said concentrate should be sufficient for most purposes.

The amount of water employed in the process of this invention is not narrowly critical and need only be that amount which is at least sufficient to solubilize that amount of the reaction products of said phosphines and said $\alpha,\beta$-unsaturated compounds resulting from the process of this invention. In general, from about 0.05 to about 2.0 volume equivalents of water based on the amount of rhodium containing starting material to be treated should be sufficient in most instances, although lower or higher amounts may be employed, if desired. Normally, about 0.3 parts by volume of water should be suitable for selectively removing the alkyldiarylphosphine from most hydroformylation reaction mediums. Moreover, while the water may be provided in any suitable manner, it is preferred to employ aqueous solutions of the $\alpha,\beta$-unsaturated compound, generally on the order of about 0.1 to about 75 percent and more preferably about 1 to about 40 percent by weight of said $\alpha,\beta$-unsaturated compound in water. When desiring only to selectively remove alkyldiarylphosphine about 1 to about 10 percent by weight of said $\alpha,\beta$-unsaturated compound in water is most preferred, while about 10 to about 40 percent by weight of said $\alpha,\beta$-unsaturated compound in water is most preferred when triarylphosphine is desired to be removed.

Further, the process of this invention can be carried out in any suitable vessel or container and does not require any special equipment. Upon completion of the phosphine-$\alpha,\beta$-unsaturated compound reaction of the process of this invention, an aqueous mixture is allowed to settle onto two distinct liquid phases, the bottom phase being the aqueous phase containing the solubilized reaction products of said triorganophosphines with said α,β-unsaturated compounds, which can be separated from the other (i.e., non-aqueous, top) liquid phase which contains the rhodium and any unreacted triorganophosphine by any suitable method, such as by draining off the bottom layer or decanting off the top layer, and the like.

The process of this invention is especially suitable in the hydroformylation field of producing aldehydes, since it provides for the selective removal of alkyl substituted phosphine from hydroformylation catalyst solutions without unduly adversely affecting the triarylphosphine and rhodium concentrations or in any other way harming the catalyst solution. Such is indeed surprising as is the fact that it has been found that the process of this invention also provides a simple means for rejuvenating the activity and increasing the life-span of the rhodium complex catalyst of a continuous hydroformylation reaction by removing all or any part of the undesirable alkyl substituted phosphine that might be present in the hydroformylation reaction medium and whose in situ build-up during said process has eventually caused an unacceptable decrease in the reactivity of said catalyst. For example, it has been found that the rate of hydroformylation, measured in terms of gram-moles per liter-hour of product produced of an alpha-olefin using a hydroformylation reaction medium which has been treated by the process of this invention is dramatically increased above that rate of hydroformylation obtained when using the corresponding hydroformylation reaction medium which has not been treated by the process of this invention. Thus, by the process of this invention the concentration level of alkyl substituted phosphine in such hydroformylation reaction mediums can be monitored and maintained at any desired limit. In general, when rejuvenating said hydroformylation catalyst, it is preferred to lower the amount of alkyl substituted phosphine present in said reaction mediums to less than about 1 percent by weight based on the total weight of the liquid rhodium containing composition, and more preferably to less than about 0.1 percent.

Moreover, the process of this invention can be performed right in the hydroformylation reactor vessel without removing the hydroformylation reaction medium from the reactor. Alternatively, the process of this invention can be carried out continuously or more preferably in a batch-type continuous manner which comprises removing all or a portion of the hydroformylation reaction medium comprising a rhodium complex catalyst, triarylphosphine, alkyl substituted phosphine and solvent for said catalyst, from the hydroformylation reactor to a separate chamber or vessel, and treating said reaction medium by the process of this invention as described above to separate and remove all or a portion of said alkyl substituted phosphine from said medium and returning the remaining non-aqueous liquid phase of said separation procedure back to said reactor. Finally, if desired, and such is recommended for commercial operations, the non-aqueous liquid phase produced by the process of this invention may be washed with any suitable aqueous alkaline solution such as a sodium bicarbonate solution to remove any excess α,β-unsaturated acidic compound that might be present, and after the alkaline solution is removed, further washed with water several times to remove any excess amount of the basic compound employed in the initial wash. After removing all of the water, the non-aqueous containing rejuvenated catalyst solution can then be reemployed in the hydroformylation process.

The process of this invention is also suitable for removing large or small amounts of triarylphosphine that may be present in said rhodium-containing compositions and/or said rhodium-containing concentrates thereof. For instance, large amounts of triarylphosphine are generally employed in continuous hydroformylation reactions designed to produce aldehydes rich in their normal isomers. However, as pointed out above, such continuous processes will eventually become spent (i.e., reach a point in which the catalyst has become so inactive that operation of the hydroformylation process is no longer economical) and the catalyst will have to be replaced. Moreover, the high cost of rhodium dictates an economical necessity to recover as much of the rhodium values as possible from such spent hydroformylation reaction mediums and any such recovery procedure will obviously require the removal of said triarylphosphine. Accordingly, as seen described herein, the removal of such large amounts of triarylphosphine can be easily accomplished by the process of this invention without any unduly large attendant loss of the rhodium present in the liquid rhodium containing composition from which said triarylphosphine is removed. Indeed, the process of this invention can be performed right in the hydroformylation reactor vessel without removing the hydroformylation reaction medium from the reactor. Of course, the process of this invention can also be carried out in any suitable chamber or vessel other than the hydroformylation reactor. Alternatively, if desired, the spent hydroformylation reaction medium can first be concentrated via distillation to very viscous rhodium complexes containing only a small amount of free triarylphosphine as described hereinabove and then said small amount of triarylphosphine removed by the process of this invention. Since the triarylphosphine is removed in the form of an aqueous solution, it can be easily disposed of without adversely affecting the environment and such is an obvious benefit to any ultimate rhodium recovery procedure.

The following examples are illustrative of the present invention and are not to be regarded as limitative. It is to be understood that all of the parts, percentages and proportions referred to herein and in the appended claims are by weight unless otherwise indicated.

EXAMPLE 1

A variety of α,β-unsaturated compounds were used to separate mixtures of propyldiphenylphosphine and triphenylphosphine. In each case the solution mixture of the phosphines was thoroughly stirred with an equal volume of a two percent by weight aqueous solution of the α,β-unsaturated compound at about 25° C. At various time periods, the resultant mixtures were allowed to settle into two distinct liquid phase layers so that the non-aqueous liquid phase (top layer) could be sampled periodically and analyzed by gas chromatography for phosphine. The results are given in Table I below.

TABLE I

Separation of Propyldiphenylphosphine and Triphenylphosphine with α,β Unsaturated Compounds

| Elapsed Time(Min) | Itaconic Acid PDPP[a]TPP[b] | Acrylic Acid PDPP[a]TPP[b] | Crotonic Acid PDPP[a]TPP[b] | Maleic Acid PDPP[a]TPP[b] | Ethyl-Propyl-Acrolein PDPP[a]TPP[b] | Acrylonitrile PDPP[a]TPP[b] |
|---|---|---|---|---|---|---|
| 0 | 1.91 9.72 | 1.91 9.72 | 1.91 9.72 | 1.91 9.72 | 1.72 9.76 | 1.70 10.00 |
| 5 | | | | | | |
| 10 | | 0.72 8.48 | 1.83 8.70 | 0.16 8.43 | | |
| 20 | | 0.32 7.92 | | 0.10 8.09 | 1.60 8.95 | |
| 80 | | | | | 1.58 8.83 | 1.49 9.30 |
| 100 | 0.95 8.44 | 0.13 7.07 | | | | |
| 120 | | | | 0.05 7.43 | | 1.37 8.10 |
| 180 | 0.66 8.23 | 0.06 6.65 | 1.30 8.54 | | | 1.34 8.00 |
| 360 | | | 1.10 8.31 | | | |
| 480 | | | 0.63 8.31 | | | |

| Elapsed Time(Min) | Ethyl Acrylate PDPP[a]TPP[b] | Maleic Anhydride PDPP[a]TPP[b] | Acrolein PDPP[a]TPP[b] | Crotonal-Dehyde PDPP[a]TPP[B] | Methacrolein PDPP[a]TPP[b] |
|---|---|---|---|---|---|
| 0 | 1.70 10.00 | 1.50 10.00 | 1.94 9.66 | 1.94 9.66 | 1.94 9.66 |
| 5 | | 0.13 8.45 | | | |
| 10 | | | | | |
| 20 | 0.91 8.76 | 0.07 6.35 | 1.44 9.17 | 1.77 9.40 | 1.72 9.00 |
| 80 | 0.30 8.85 | | | | |
| 100 | 0.17 8.84 | | | | |
| 120 | | | | | |
| 180 | 0.07 8.44 | | | | |

[a] wt % Propyldiphenylphosphine
[b] wt % Triphenylphosphine

EXAMPLE 2

A mixture of six different phosphines was prepared by dissolving 0.2 grams each of (1) diphenylphosphine, (2) iso-propyldiphenylphosphine, (3) propyldiphenylphosphine, (4) butyldiphenylphosphine, and (5) dipropylphenylphosphine and 1.0 gram of (6) triphenylphosphine in Texanol ® solvent, a mixture of butyraldehyde trimers. The mixture was then stirred for about 16 minutes with an equal volume of a two percent by weight aqueous solution of maleic acid and the mixture allowed to settle into two distinct liquid phases. The bottom aqueous phase was then separated from the non-aqueous phase and the non-aqueous phase analyzed for phosphines by gas chromatography. The amount of each phosphine extracted from the initial mixture is given in Table II below in terms of millimoles extracted.

TABLE II

| Phosphine | MMoles Initial | MMoles Final | % Extracted |
|---|---|---|---|
| Dipropylphenyl | 1.03 | 0.06 | 94.3 |
| Propyldiphenyl | 0.88 | 0.55 | 37.5 |
| Iso-Propyldiphenyl | 0.88 | 0.66 | 25.0 |
| Butyldiphenyl | 0.83 | 0.50 | 39.8 |
| Triphenyl | 3.82 | 3.74 | 2.1 |
| Diphenyl | 1.08 | 1.05 | 2.8 |

From the table, it can be seen that the extraction corresponds to basicity of the phosphines, that is dipropylphenylphosphine > propyldiphenylphosphine ~ isopropyldiphenylphosphine ~ butyldiphenylphosphine > diphenylphosphine ~ triphenylphosphine.

EXAMPLE 3

A solution mixture containing about 2 weight percent propyldiphenylphosphine and about 10 weight percent triphenylphosphine was treated with a series of aqueous maleic acid solutions containing 1 to 5 mole equivalents of maleic acid per mole equivalent of propyldiphenylphosphine. The concentration of maleic acid in each solution was 2.0 weight percent. Each extraction involved stirring the phosphine mixture with an aqueous maleic acid solution for five minutes at 25° C., allowing the resultant mixture to settle into two distinct liquid phases, separating the bottom aqueous phase from the non-aqueous phase and analyzing said non-aqueous phase by gas chromatography for propyldiphenylphosphine.

TABLE III

| Run No. | Mole Ratio of PDPP to Maleic Acid | Vol. Equivalent Ratio of Water to Phosphine Mixt. | Relative Wt. % PDPP Extracted | Relative Wt % TPP Extracted |
|---|---|---|---|---|
| 1 | 1:1 | 1:2 | 64.3 | 4.9 |
| 2 | 2:1 | 1:1 | 84.7 | 5.5 |
| 3 | 3:1 | 1.5:1 | 90.5 | 6.8 |
| 4 | 4:1 | 2:1 | 92.3 | 7.3 |
| 5 | 5:1 | 2.5:1 | 94.5 | 9.2 |

PDPP = Propyldiphenylphosphine
TPP = Triphenylphosphine

EXAMPLE 4

A phosphine solution containing 4.4 millimoles of both propyldiphenylphosphine and triphenylphosphine was stirred at about 25° C. with about 0.5 parts by volume of an aqueous solution containing 0.4 mole equivalents of maleic acid per mole equivalent of propyldiphenylphosphine until all of the maleic acid was consumed. The resultant mixture was allowed to settle into two distinct liquid layers and the bottom aqueous layer was separated from the non-aqueous layer. Gas chromatographic analysis of the non-aqueous layer showed that 1.6 millimoles of propylphenylphosphine and 0.3 millimoles of triphenylphosphine had been extracted. Thus the selectivity ratio toward propyldiphenylphosphine extraction over triphenylphosphine was 5.3 to 1.

EXAMPLE 5

A hydroformylation reaction medium, which contained a mole ratio of triphenylphosphine to propyldiphenylphosphine of 5.7 to 1 and which had a catalyst activity measured in terms of the amount of product produced of 0.40 gram-moles per liter-hour and which was derived from a continuous hydroformylation process to produce butyraldehyde rich in its normal isomer by hydroformylating propylene with carbon monoxide and hydrogen, said hydroformylation medium further comprising a rhodium complex catalyst consisting essentially of rhodium complexed with carbon monoxide, triphenylphosphine and/or propyldiphenylphosphine, free triphenylphosphine, free propyldiphenylphosphine and as the solvent for said catalyst the liquid high boiling condensation products of said butyraldehyde, was treated with a series of equal volume aqueous maleic acid solutions containing various amounts of maleic acid for various contact time periods at about 25° C. to extract propyldiphenylphosphine, said variables being set forth in Table IV below. Each extraction consisted of thoroughly mixing (i.e. stirring) the hydroformylation medium with the aqueous maleic acid solution for the prescribed period of time, allowing the resultant mixture to separate into two distinct liquid phase layers and removing the bottom aqueous phase layer from the non-aqueous phase layer. Each recovered non-aqueous liquid phase was then analyzed for rhodium by atomic absorption and for triphenylphosphine and propyldiphenylphosphine by gas chromatography and then used to hydroformylate propylene to determine catalyst reactivity. The results are summarized in Table IV below.

TABLE IV

| Maleic Acid Concentration[a] | Contact Time (Minutes) | TPP/PDP Ratio[b] | Rhodium Lost[c] | Catalyst[d] Reactivity (g-moles/1-hr) |
|---|---|---|---|---|
| 0.5 | 5 | 7.4:1 | 0.2 | 0.45 |
| 0.5 | 10 | 10.6:1 | 0.2 | 0.52 |
| 1.0 | 1 | 16.9:1 | 0.2 | 0.55 |
| 1.0 | 5 | 19.2:1 | 0.2 | 0.57 |
| 1.0 | 10 | 20.6:1 | 0.2 | 0.62 |
| 2.0 | 1 | 28.1:1 | 0.2 | 0.65 |
| 2.0 | 5 | 36.3:1 | 0.2 | 0.69 |
| 2.0 | 10 | 39.8:1 | 0.2 | 0.74 |

[a] = wt. % of maleic acid in aqueous solution.
[b] = molar ratio of triphenylphosphine to propyldiphenylphosphine
[c] = wt. % of rhodium values lost
[d] = amount of product produced in terms of gram-moles per liter-hour with the treated hydroformylation medium.

As seen by the above results in every case rhodium losses were minimal, while the hydroformylation rate (catalyst activity) increased as the triphenylphosphine to propyldiphenylphosphine ratio increased thereby demonstrating the beneficial results obtained upon removing propyldiphenylphosphine from the starting hydroformylation medium.

EXAMPLE 6

A hydroformylation reaction medium, which contained a mole ratio of triphenylphosphine to propyldiphenylphosphine of 8.7 to 1 and which had a catalyst activity measured in terms of the amount of product produced of 0.245 gram-moles per liter-hour and which was derived from a continuous hydroformylation process to produce butyraldehyde rich in its normal isomer by hydroformylating propylene with carbon monoxide and hydrogen, said hydroformylation further comprising a rhodium complex catalyst consisting essentially of rhodium complexed with carbon monoxide, triphenylphosphine and/or said propyldiphenylphosphine, free triphenylphosphine, free propyldiphenylphosphine, and as the solvent for said catalyst the liquid high boiling condensation products of said butyaldehyde, was stirred (mixed) with about 0.5 parts by volume of about a 3.7 percent by weight aqueous solution of maleic acid (about 3 moles equivalents of maleic acid per mole equivalent of propyldiphenylphosphine in said hydroformylation medium was used). Said mixing took place right in the hydroformylation reactor and was carried out for thirty minutes at about 60° C. The resultant mixture was then allowed to settle into two distinct liquid layers and the aqueous bottom layer was removed. The remaining non-aqueous layer was then washed in the reactor with an aqueous sodium bicarbonate solution and then with water to remove any residual maleic acid and sodium bicarbonate. Upon removal of the aqueous wash phases the remaining non-aqueous solution was analyzed by gas chromatography and found to contain a triphenylphosphine to propyldiphenylphosphine molar ratio of about 83.5 to 1 and was further used to hydroformylate propylene to determine catalyst reactivity. The rate of hydroformylation using said treated and recovered non-aqueous hydroformylation medium was 0.400 gram-moles per liter-hour of product produced which corresponded to a rate enhancement of 63 percent above the lower rate of 0.245 gram-moles per liter-hour of product produced for the initial untreated hydroformylation reaction medium.

EXAMPLE 7

Ten milliliters of a solution containing 10.0 weight percent triphenylphosphine and 2.0 weight percent propyldiphenylphosphine in Texanol ® solvent (a mixture of butyraldehyde trimers) was contacted and stirred for thirty minutes under nitrogen with ten milliliters of a 40 percent by weight aqueous maleic acid solution. Then the mixture was allowed to settle into two distinct liquid phases and the bottom aqueous phase layer separated from the non-aqueous top-phase layer. Gas chromatographic analysis of the non-aqueous liquid phase show it to contain no propyldiphenylphosphine and less than about 0.5 percent by weight of triphenylphosphine.

EXAMPLE 8

A hydroformylation reaction medium which was derived from a continuous hydroformylation process to produce butyraldehyde rich in its normal isomer by hydroformylating propylene with carbon monoxide and hydrogen in the presence of a solubilized rhodium hydroformylation complex catalyst and which medium contained about 9.9 grams of propyldiphenylphosphine and about 86.6 grams of triphenylphosphine was distilled up to 160° C. at 4 mm Hg. to remove the volatile compounds of said medium. Under these conditions, no phosphines were distilled from said medium. The remaining hydroformylation medium was then cooled to 60° C. under atmospheric pressure and then was contacted and stirred with about 0.5 parts by volume of a 30 percent by weight aqueous maleic acid solution for one hour, and the reaction mixture allowed to settle into two distinct liquid phase layers. The bottom aqueous phase was then separated from the non-aqueous liquid top phase and said non-aqueous liquid phase was shown by gas chromatography to contain no propyldiphenylphosphine and only 2.4 grams of triphenylphosphine. A second treatment of the non-aqueous liquid phase obtained from the first treatment with a second 30 percent by weight aqueous maleic acid solution in the same manner as given above reduced the triphenylphosphine content of the non-aqueous phase to only 0.2 grams or 0.2 percent of the amount of triphenylphosphine present initially in the hydroformylation reaction medium.

Various modifications and variations of this invention will be obvious to a worker skilled in the art and it is to be understood that such modifications and variations are to be included within the purview of this application and the spirit and scope of the appended claims.

What is claimed is:

1. A process for removing triorganophosphine selected from the class consisting of triarylphosphine and alkyl substituted phosphine of the formula

 (I)

wherein R is an alkyl radical, R' is an alkyl or aryl radical and R" is an aryl radical from a liquid rhodium containing composition or a rhodium containing concentrate of said composition, said process comprising (1) mixing (a) a rhodium containing composition comprising a rhodium complex hydroformylation catalyst, triarylphosphine and alkyl substituted phosphine of formula (I) above, or (b) a rhodium containing concentrate of said composition, with an α,β-unsaturated compound selected from the group consisting of compounds having the formula

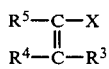

wherein X is a radical selected from the group consisting of

—CN, —Cl, —Br, —I, —NO₂, and —OR⁷; R⁶ is a radical selected from the group consisting of hydrogen, alkyl, aryl, hydroxy, alkoxy, amino and halogen; R⁷ is an alkyl or aryl radical; and R³, R⁴ and R⁵ are each individually radicals selected from the group consisting of hydrogen, alkyl, aryl, X radicals as defined above and —CH₂X radicals wherein X is the same as defined above; and wherein R⁴ and R⁵ taken together can form an alkylene group having from 2 to 8 carbon atoms; and anhydrides of the carboxylic acids of said α,β-unsaturated formula compounds;

(2) allowing an aqueous mixture of said step (1) to settle into two distinct liquid phases, and (3) separating the aqueous phase which contains the solubilized reaction products of the alkyl substituted phosphine and/or triarylphosphine present in said composition or concentrate with said α,β-unsaturated compound from the non-aqueous liquid phase resulting from said steps (1) and (2); and wherein the molar ratio of the amount of said α,β-unsaturated compound employed to the total amount of the alkyl substituted phosphine and/or triarylphosphine present in said composition or concentrate is at least 0.1 to 1; and wherein the amount of water employed is at least sufficient to solubilize that amount of the reaction products of said phosphines with said α,β-unsaturated compound resulting from said steps (1) and (2).

2. A process as defined in claim 1 wherein a rhodium containing composition comprising a rhodium complex hydroformylation catalyst, triarylphosphine and alkyl substituted phosphine of formula (I) is mixed, in the presence of water, with said α,β-unsaturated compound.

3. A process as defined in claim 2, wherein the molar ratio of the amount of said α,β-unsaturated compound employed to the total amount of said alkyl substituted phosphine present in said rhodium containing composition is at least about 0.1 to 1, while the molar ratio of said α,β-unsaturated compound employed to the total amount of said triarylphosphine present in said rhodium containing composition is less than 1 to 1.

4. A process as defined in claim 3, wherein the rhodium containing composition comprises a rhodium complex catalyst consisting essentially of rhodium complexed with carbon monoxide, triarylphosphine, and/or alkyl substituted phosphine of the formula

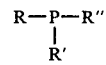

wherein R, R' and R" are the same as defined above, free triarylphosphine and free alkyl substituted phosphine of the formula

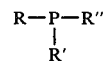

wherein R, R' and R" are the same as defined above.

5. A process as defined in claim 4, wherein the triarylphosphine is triphenylphosphine and wherein said step (1) is conducted at a temperature of about 0° C. to about 150° C.

6. A process as defined in claim 5, wherein said liquid composition also contains an organic solvent for said catalyst.

7. A process as defined in claim 6, wherein the α,β-unsaturated compound is maleic acid or maleic anhydride.

8. A process as defined in claim 7, wherein the alkyl substituted phosphine is selected from the group consisting of ethyldiphenylphosphine, propyldiphenylphosphine and butyldiphenylphosphine.

9. A process as defined in claim 8, wherein said step (1) is conducted at a temperature of about 25° C. to about 80° C.

10. A process as defined in claim 5, wherein the α,β-unsaturated compound is employed in the form of an aqueous solution containing from about 0.1 to about 75 percent by weight of said α,β-unsaturated compound.

11. A process as defined in claim 10, wherein about 0.5 to about 2.0 volume equivalents of water are employed based on the amount of said liquid composition employed.

12. A process as defined in claim 11, wherein the aqueous solution contains about 1 to about 10 percent by weight of said α,β-unsaturated compound and wherein the amount of said α,β-unsaturated compound employed is about 1 to about 5 mole equivalents per mole equivalent of the total amount of said alkyl substituted phosphine present in said liquid composition.

13. A process as defined in claim 12, wherein the α,β-unsaturated compound is a carboxylic acid and wherein at least $R^3$ and $R^4$ is hydrogen.

14. A process as defined in claim 12, wherein the α,β-unsaturated compound is an anhydride of a carboxylic acid and $R^4$ is hydrogen.

15. A process as defined in claim 11, wherein the α,β-unsaturated compound is maleic acid or maleic anhydride and wherein step (1) is conducted at a temperature of about 25° C. to about 80° C.

16. A process as defined in claim 15, wherein said liquid composition also contains an organic solvent for said catalyst.

17. A process as defined in claim 16, wherein the alkyl substituted phosphine is selected from the group consisting of ethyldiphenylphosphine, propyldiphenylphosphine and butyldiphenylphosphine.

18. A process as defined in claim 17, wherein the alkyl substituted phosphine is propyldiphenylphosphine and the α,β-unsaturated compound is maleic acid.

19. A process as defined in claim 2, wherein the molar ratio of α,β-unsaturated compound employed to the total amount of the alkyl substituted phosphine and triarylphosphine present in said composition is at least 1 to 1.

20. A process as defined in claim 19, wherein the rhodium containing composition comprises a rhodium complex catalyst consisting essentially of rhodium complexed with carbon monoxide, triarylphosphine, and/or alkyl substituted phosphine of the formula

wherein R, R' and R" are the same as defined above, free triarylphosphine and free alkyl substituted phosphine of the formula

wherein R, R' and R" are the same as defined above.

21. A process as defined in claim 20, wherein the triarylphosphine is triphenylphosphine and wherein said step (1) is conducted at a temperature of about 0° C. to about 150° C.

22. A process as defined in claim 21, wherein said liquid composition also contains an organic solvent for said catalyst.

23. A process as defined in claim 22, wherein the α,β-unsaturated compound is maleic acid or maleic anhydride.

24. A process as defined in claim 23, wherein the alkyl substituted phosphine is selected from the group consisting of ethyldiphenylphosphine, propyldiphenylphosphine and butyldiphenylphosphine.

25. A process as defined in claim 24, wherein said step (1) is conducted at a temperature of about 25° C. to about 80° C.

26. A process as defined in claim 21, wherein the α,β-unsaturated compound is employed in the form of an aqueous solution containing from about 0.1 to about 75 percent by weight of said α,β-unsaturated compound.

27. A process as defined in claim 26, wherein about 0.5 to about 2.0 volume equivalents of water are employed based on the amount of said liquid composition employed.

28. A process as defined in claim 27, wherein the aqueous solution contains about 10 to about 40 percent by weight of said α,β-unsaturated compound and wherein the amount of said α,β-unsaturated compound employed is about 1 to about 5 mole equivalents per mole equivalent of the total amount of said alkyl substituted phosphine and said triarylphosphine present in said liquid composition.

29. A process as defined in claim 28, wherein the α,β-unsaturated compound is a carboxylic acid and wherein at least $R^3$ and $R^4$ is hydrogen.

30. A process as defined in claim 28, wherein the α,β-unsaturated compound is an anhydride of a carboxylic acid and $R^4$ is hydrogen.

31. A process as defined in claim 27, wherein the α,β-unsaturated compound is maleic acid or maleic anhydride and wherein step (1) is conducted at a temperature of about 25° C. to about 80° C.

32. A process as defined in claim 31, wherein said liquid composition also contains an organic solvent for said catalyst.

33. A process as defined in claim 32, wherein the alkyl substituted phosphine is selected from the group consisting of ethyldiphenylphosphine, propyldiphenylphosphine and butyldiphenylphosphine.

34. A process as defined in claim 33, wherein the alkyl substituted phosphine is propyldiphenylphosphine and the α,β-unsaturated compound is maleic acid.

35. A process as defined in claim 1, wherein a rhodium containing concentrate of said rhodium containing composition is mixed with said α,β-unsaturated compound.

36. A process as defined in claim 35, wherein said rhodium containing composition comprises a rhodium complex catalyst consisting essentially of rhodium complexed with carbon monoxide, triarylphosphine, and/or alkyl substituted phosphine of the formula

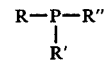

wherein R, R' and R" are the same as defined above, free triarylphosphine and free alkyl substituted phosphine of the formula

wherein R, R' and R" are the same as defined above.

37. A process as defined in claim 36, wherein said rhodium containing composition also contains an organic solvent for said catalyst.

38. A process as defined in claim 37 wherein the concentrate is mixed with said α,β-unsaturated compound in the presence of water.

39. A process as defined in claim 38 wherein the triarylphosphine is triphenylphosphine and wherein the α,β-unsaturated compound is maleic acid or maleic anhydride.

40. A process as defined in claim 37, wherein said concentrate contains from about 1000 to about 50,000 ppm of rhodium calculated as free metal; and wherein the molar ratio of said α,β-unsaturated compound employed to the total amount of said triarylphosphine and any said alkyl substituted phosphine present in said concentrate is at least 1 to 1.

41. A process as defined in claim 40, wherein said concentrate is dissolved in a solvent and then mixed with said α,β-unsaturated compound in the presence of water.

42. A process as defined in claim 41, wherein the triarylphosphine is triphenylphosphine and wherein the α,β-unsaturated compound is employed in the form of an aqueous solution containing about 10 to about 40 percent by weight of said α,β-unsaturated compound and wherein the amount of said α,β-unsaturated compound employed is about 1 to about 25 mole equivalents per mole equivalent of the total amount of said triarylphosphine and any said alkyl substituted phosphine present in said rhodium containing concentrate.

43. A process as defined in claim 42 wherein said α,β-unsaturated compound is maleic acid or maleic anhydride.

* * * * *